(12) United States Patent
Wurzbach et al.

(10) Patent No.: US 10,627,387 B1
(45) Date of Patent: Apr. 21, 2020

(54) METHOD AND RELATED DEVICE FOR GREASE EVALUATION

(71) Applicant: York Laboratories, LLC, York, PA (US)

(72) Inventors: Richard Wurzbach, Brogue, PA (US); Evan Bupp, Red Lion, PA (US); Richard J. Janosky, Jr., Dover, PA (US)

(73) Assignee: York Laboratories, LLC, York, PA (US)

( * ) Notice: Subject to any disclaimer, the term of this patent is extended or adjusted under 35 U.S.C. 154(b) by 0 days.

(21) Appl. No.: 16/006,430

(22) Filed: Jun. 12, 2018

Related U.S. Application Data

(63) Continuation-in-part of application No. 15/135,116, filed on Apr. 21, 2016, now abandoned.

(60) Provisional application No. 62/150,518, filed on Apr. 21, 2015.

(51) Int. Cl.
*G01N 33/30* (2006.01)
*G01J 3/28* (2006.01)
*G01N 21/31* (2006.01)

(52) U.S. Cl.
CPC .............. *G01N 33/30* (2013.01); *G01J 3/28* (2013.01); *G01N 21/314* (2013.01)

(58) Field of Classification Search
CPC .......... G01N 33/30; G01N 21/314; G01J 3/28
See application file for complete search history.

(56) References Cited

U.S. PATENT DOCUMENTS 5,309,213 A * 5/1994 Desjardins ........... G01N 21/534
356/246
5,750,998 A * 5/1998 Goldman ............... G01N 21/51
250/343

\* cited by examiner

*Primary Examiner* — Hwa Andrew Lee
(74) *Attorney, Agent, or Firm* — Hooker & Habib, P.C.

(57) ABSTRACT

A method for evaluating the condition of grease includes submitting a sample of grease to light from a spectrophotometer, passing the light through the sample along a light path, and analyzing the color or spectrum of the light after emerging from the light path. The length of the light path can be varied as needed to enable translucent or very light-colored greases and greases that are dark provide useable data from the light passing through the grease.

16 Claims, 4 Drawing Sheets

METHOD AND RELATED DEVICE FOR GREASE EVALUATION

RELATED APPLICATIONS

This application claims the benefit of the following pending US patent application and provisional patent application: co-pending U.S. patent application Ser. No. 15/135,116 "Method for Evaluating a Sample of Grease" filed Apr. 21, 2016 which in turn claims the benefit of U.S. Provisional Patent Application No. 62/150,518 "Method for Evaluating Changing Inservice Grease Properties and Contaminants Using Absorbance Spectroscopy of Visible Light Measured Through a Transparent Sampling Device" filed Apr. 21, 2015, which priority applications are incorporated by reference as if fully set forth herein.

FIELD OF THE DISCLOSURE

This disclosure relates to methods for evaluating samples of grease.

BACKGROUND OF THE DISCLOSURE

The term "grease" as used herein refers to a semisolid lubricant.

It is estimated that 90% of all machine bearings are lubricated by grease. While oil analysis is a widespread tool for monitoring bearing and lubricated component health of important oil lubricated equipment, grease analysis is not generally adopted in a similar manner for important grease lubricated machines. Analyzing a sample of grease taken from a grease-lubricated bearing sometimes is performed to pinpoint the cause of bearing problems in failure analysis. However, the ability to analyze grease has been historically limited by the inability to easily obtain representative samples of the grease in a sufficient quantity to perform cost-effective and meaningful analysis.

Wurzbach U.S. Pat. No. 7,984,661 discloses a method of obtaining a sample of grease from a machine and into a container for later analysis. The Wurzbach patent is incorporated by reference herein.

A known method for analyzing grease is to extrude a sample of the grease having a fixed, predetermined thickness from the container through a fixed die and onto a substrate, and exposing the fixed layer of grease to a light source. The light passes through the grease and through the substrate, and the light transmitted through the grease and substrate is detected by a detector. The spectrum of the light reaching the detector is compared to the spectrum obtained from a reference sample of grease. The differences in the spectrums relates to changes in the state or condition of the grease.

A problem with the known method for grease analysis is that grease has a tendency to "go dark" and substantially darken over the operating lifetime of the grease. The grease may go dark because of contamination or other causes indicating a bearing or machine problem, or the grease may go dark merely because of aging of the grease over the operating lifetime of the grease with normal operation of the bearing or machine (and without darkening caused by contamination or any other undesirable cause of grease change indicating a bearing or machine problem).

Grease that has gone dark may not transmit enough light to through the grease to be detected by the sensor. Or there may be some light transmitted through the grease but not enough light is detected to enable accurate determination of the color or color spectrum of the light passing through the grease. In either case the detector may report the color as being black or so close to black that meaningful comparison to a base color cannot be made.

Increasing the intensity of the light to increase light transmittal through the darkened grease does not solve the problem of analyzing grease that has gone dark.

Experiments with increasing light intensity found that useful results were often not obtained. It was theorized after the method disclosed herein was developed that the increased light intensity increases scattering effects. The scattering and the attenuation of light due to particulates or other constituents decreases the signal-to-noise ratio significantly to render the result indistinguishable for the purposes of making a meaningful measurement.

SUMMARY OF THE DISCLOSURE

Disclosed is a method and related device for evaluating the condition of grease using a light source that enables evaluation of greases that have gone dark as well as being able to measure and compare sufficiently translucent greases.

A representative sample of the grease to be evaluated is obtained from a bearing or machine of interest and is evaluated without otherwise treating or modifying the grease. The grease is exposed to light of a standard intensity issued from a light source such as a spectrophotometer, the light passing through the grease sample. The light may include all the frequencies of the visible spectrum.

The light passing through the grease sample travels a first predetermined path length through the grease.

The light after traveling through the grease is detected by a spectrometer or color sensor of the spectrophotometer that provides spectrum and/or color information of the detected light.

The spectrophotometer provides objective data concerning the color of the grease. Changes in the color or color spectrum of the light passing through the grease over time reflects changes in the state or condition of the grease caused by aging of the grease or changes in the grease caused by the bearing or machine environment (overheating, contamination, or the like).

In a first embodiment of the disclosed method if the grease has gone dark and there is or would be insufficient light reaching the detector after traveling the first path length through the grease for meaningful analysis, the path length used for evaluation is reduced to a second path length that is less than the first path length. The reduction in path length increases the light reaching the detector without changing the intensity of the light received by the grease sample. The second path length may also be a predetermined path length.

For example, the color measurement of a sample of grease that had gone dark having a first sample thickness reported an RGB color of 46 49 43 (visually, black). Reducing the sample thickness resulted in an RGB color measurement of 110 115 79, corresponding to a dark green color and enabled evaluation of the grease sample.

Grease that is sufficiently translucent may exhibit "bleaching" when attempting to evaluate the grease using a light source. There is so much transmitted light that the color or spectrum of the light at the detector is not affected sufficiently by the grease to provide useful results. But reducing light intensity to reduce light transmittal does not solve the bleaching problem. Again it was theorized that reducing the light intensity changes the percentage of light reflection, thereby preventing effective correlation of changes in color or spectrum to changes in grease state.

A second embodiment of the disclosed method may be used when evaluating translucent grease that exhibits bleaching. The path length of the light passing through the grease is increased to a third path length greater than the first path length. The third path length may also be a predetermined path length. Generally this third path length becomes the default path length when the evaluation is first performed, allowing successively decreasing path lengths to be used for evaluating the optimal path length for a given grease.

In variants of these methods the light transmitted through the grease sample is reflected off of a reflective surface to pass through the grease sample a second time before reaching the detector. For example, the light may first pass through a front surface of the grease sample before reaching a back surface of the grease sample, the front and back surfaces being separated by the thickness of the grease sample. The light reaching the back surface may then be reflected to pass through the grease sample again, thereby effectively doubling the effective path length of the light through the grease sample. The light emerges from the front surface and reaches the detector.

The reflective surface in embodiments of the disclosed method is in intimate contact with the back surface of the grease sample, thereby reducing scattering of the reflected light and effectively eliminating reflection of light re-entering the grease sample.

In embodiments the reflective surface is formed as a flat planar surface of a sheet, film, foil, mirror, or the like, such as a thin aluminum foil. The effective light path may be selectively varied by varying the thickness of the grease sample on the reflective sheet.

The front surface of the grease sample may in embodiments be disposed against a flat planar surface of a transparent sheet, film, foil, or the like, such as a thin, transparent plastic sheet. The grease sample is sandwiched between the transparent sheet and the reflective sheet, the sheets establishing the thickness of the grease sample. Light from the spectrometer enters the grease sample through the transparent sheet, passes through the thickness of the grease sample, is then reflected off the reflected sheet, and passes through the thickness of the grease sample a second time before emerging through the transparent sheet and being detected by the detector.

In embodiments of a device to carry out the disclosed method, one of the transparent sheet and the reflective sheet is fixed in position and the other sheet is movably mounted for selective adjustment of the spacing between the sheets. A grease sample is placed onto the fixed sheet, and the movable sheet is moved into contact with the grease sample until the movable sheet is spaced the desired distance from the reflective sheet. The grease sample is pressed or sandwiched between the sheets as the movable sheet moves towards the fixed sheet, thereby insuring the front and back surfaces of the grease sample are in intimate contact with both the movable sheet and the fixed sheet during the measurement. The light source is then actuated to transmit light through the grease sample as previously described, and the spectrophotometer detects the transmitted light, and determines the color and/or the spectrum of the light received at the detector.

In variant embodiments of the device, the transparent sheet is the fixed sheet, and the reflective sheet is the movable sheet. The transparent sheet is mounted on a support surface of the spectrometer. The support surface is spaced a predetermined distance from the light source and the spectrophotometer has an opening that enables light emitted from the light source to pass through the transparent sheet on the spectrophotometer support surface. The support surface opening also enables the reflected light emerging from the transparent sheet to reach the detector of the spectrometer.

The reflective sheet may be mounted on an end of a movable arm that selectively spaces the reflective sheet from the transparent sheet. The arm in embodiments may be the ram of an arbor press or lever press. A suitable press is the Model AP-810 lever press available from Janesville Tool & Manufacturing, Inc., Janesville, Wis. When the ram is lowered to the end of the press stroke, the reflective sheet is spaced from the transparent sheet the necessary distance to achieve the necessary thickness of the grease sample and thereby the desired path length.

The stroke length of the press may be adjustable to selectively vary the spacing between the sheets when the ram is lowered to the end of the stroke. Alternatively, shims or spacers can be placed beneath the spectrometer to vary the distance between the reflective sheet and the support surface (and thereby the transparent sheet) when the ram is in its lowered position.

In possible embodiments of the device the spectrophotometer forms part of the portable color sensor disclosed in Sheriden, U.S. Pat. No. 9,891,109, which patent is incorporated by reference as if fully set forth herein. The portable color sensor is available commercially as the NIX® PRO color sensor manufactured by Nix Sensor Ltd., Hamilton, Ontario, Canada.

The portable color sensor includes a flat outer surface that is normally pressed against a surface whose color is to be measured. In its use with the present method, the sensor is set on the base of the press or on a fixed spacer which is placed on the base of the press. The outer surface defines an upper horizontal surface of the sensor. The transparent sheet is placed on the sensor's outer surface. The transparent sheet protects the sensor from the grease sample while still allowing the grease sample to be exposed to the sensor's light source.

The color sensor's spectrophotometer light source includes a number of LEDs disposed around an optical tube that extends vertically away from the spectrometer's detector (a color sensor). The LED output is a broad parallel spectrum of all wavelengths of visible light. The light output is directed to illuminate the grease sample at about a 45-degree angle from the vertical, minimizing specular reflections from reaching the color sensor.

It has been found that sufficient light is transmitted through the grease sample from the LEDs to obtain meaningful color data results. The NIX® PRO color sensor can output the color data to different color spaces, including HSL, LAB, XYZ, CIE, RGB, CMYK color spaces, or PANTONE® units. LE values, which are differences in L*, a*, b* values between samples or between a sample and a base color can also be obtained. The data from the color sensor can be transmitted wirelessly or through a cable.

Generally speaking, different color spaces extend over different, but substantially overlapping, ranges of the visible spectrum. Other color spaces are known and the color data can be converted for use in those other color spaces (for example, the HWB color space) if desired.

Other objects and features of the disclosure will become apparent as the description proceeds, especially when taken in conjunction with the accompanying drawing sheets illustrating one or more non-limiting embodiments.

DETAILED DESCRIPTION

Figure 1:
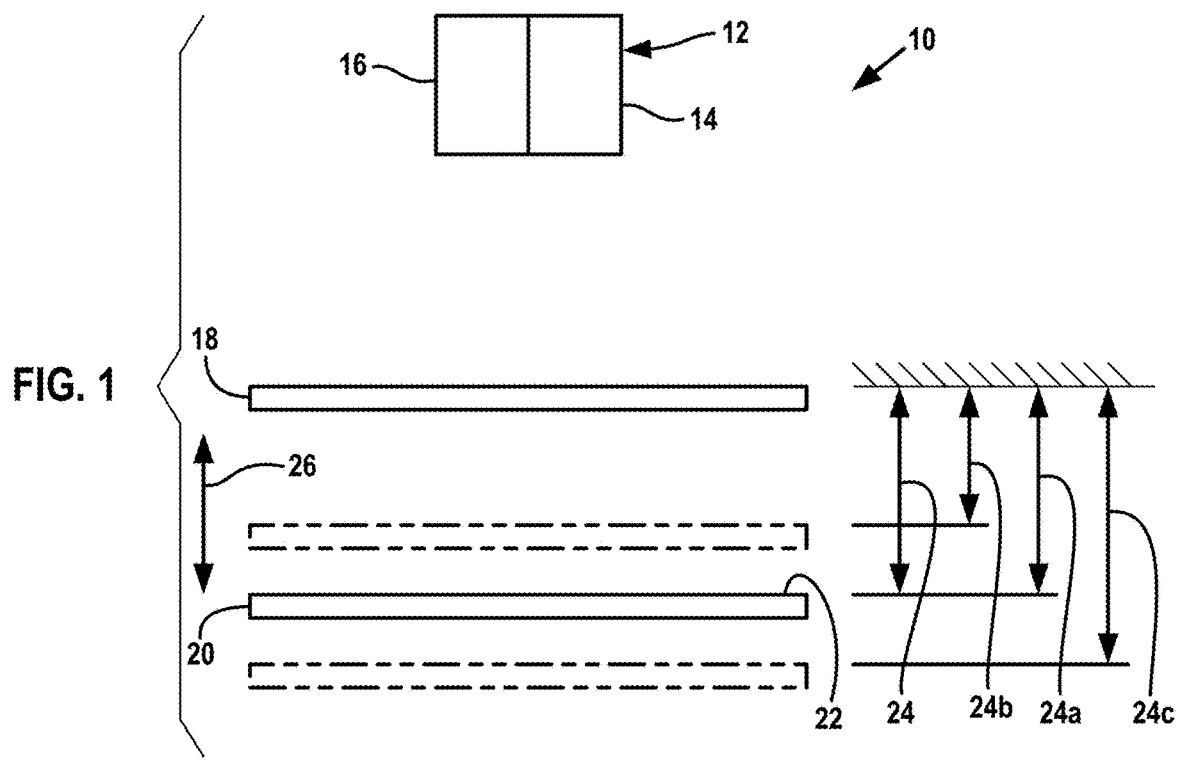
FIG. 1 is a schematic view of an embodiment of a device for evaluating grease in accordance with this disclosure.

FIG. 1 illustrates a device 10 for evaluating a grease sample. The device includes a spectrophotometer 12 having a light source 14 and a light detector 16, and horizontal, parallel first and second sheets 18, 20 that are vertically spaced apart from one another.

The spectrophotometer is disposed on one side of the first sheet 18. The first sheet is a thin, flat, transparent plastic sheet. The second sheet 20 is disposed on the other side the first sheet and is a thin, flat, reflective sheet made of aluminum. The second sheet has a highly light-reflective upper surface 22 facing the spectrophotometer 12. The first and second sheets are parallel with one another and the opposing faces of the sheets are vertically spaced a uniform distance apart from one another by a space or gap 24 (which in using the illustrated device 10 can be selected by a user to be a gap 24a, a gap 24b, or a gap 24c).

The first and second sheets 18, 20 are vertically movable with respect to one another to selectively change or adjust the vertical gap 24. In the illustrated embodiment the first sheet 18 is fixed vertically with respect to the spectrophotometer 12. The second sheet 20 is movable vertically with respect to the spectrophotometer 12 along a vertical axis 26. The second sheet is positioned with respect to the first sheet as shown in solid lines in FIG. 1 to define the first, nominal gap 24a. The second sheet can also be selectively positioned with respect to the first sheet as shown in phantom lines in FIG. 1 to define the second, narrower gap 24b, and the third, wider gap 24c.

In the illustrated embodiment the nominal gap 24a is 10 mils (10 one-thousandths of an inch or 0.254 millimeters), the narrower gap 24b is 25 mils (25 one-thousandths of an inch or 0.635 millimeters), and the wider gap 24c is 35 mils (35 one-thousands of an inch or 0.889 millimeters). Each of the gaps can vary from the illustrated embodiment in other embodiments of the device 10, The light source 14 emits light of substantially uniform intensity in all or substantially all the wavelengths of the visible light spectrum. The light source 14 is positioned so that the emitted light passes through the transparent sheet 18 and into the gap 24, reflects off the reflective surface 22 and back through the gap 24. The light detector 16 is positioned to detect the light that has been reflected from the reflective surface 22. The light detector determines the spectrum of the received light as a function of wavelength and/or determines the color of the reflected light in accordance with a color space. The spectrophotometer transmits the detector data by wired or wireless transmission to a computer (not shown) for data analysis, data storage, and display.

To evaluate a grease sample, the transparent sheet 18 is first removed for convenient access to the reflective sheet 20. The reflective sheet 20 is initially positioned vertically away from the spectrophotometer 12 below the position defining the gap 24c. A grease sample 27 (see FIG. 2) is placed on the transparent sheet and the transparent sheet is restored in place with the grease sample between the sheets. The amount of grease is sufficient to completely fill the gap 24 as the sheets are squeezed together to the first gap 24c.

Figure 2:
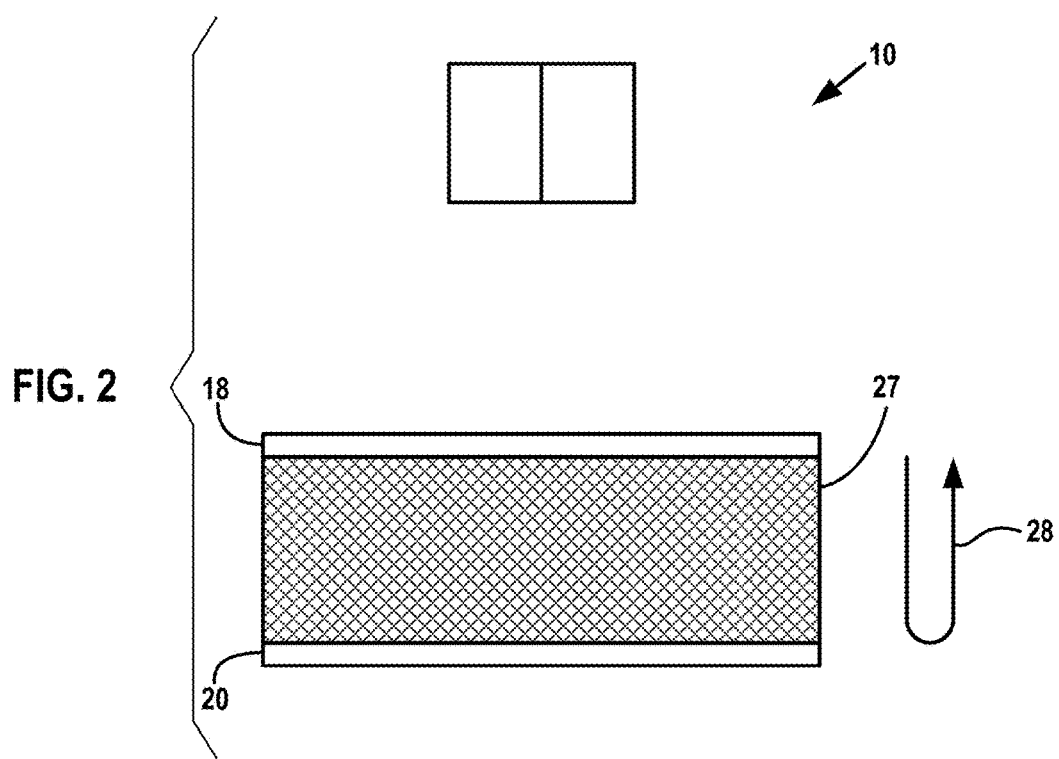
FIG. 2 illustrates the device shown in FIG. 1 when evaluating a sample of grease.

The reflective sheet 20 is then moved vertically until the gap between the sheets is established at the first gap 24c as shown in FIG. 2. The amount of grease is sufficient to completely fill the gap 24c. The grease sample 27 is sandwiched between and thereby compressed between the sheets 18, 20 to assure intimate contact of the grease with the facing surfaces of the sheets.

The light source 14 emits light that passes through the gap 24c two times before reaching the detector 16. The length of the light path 28 the light travels through the grease sample is directly proportional to the magnitude of the gap 24 and for practical purposes can be considered equal to twice the vertical spacing between the sheets 18, 20. Thus for the grease evaluation illustrated in FIG. 2 the light path through the grease sample is twice the magnitude of the gap 24c.

Figure 3:
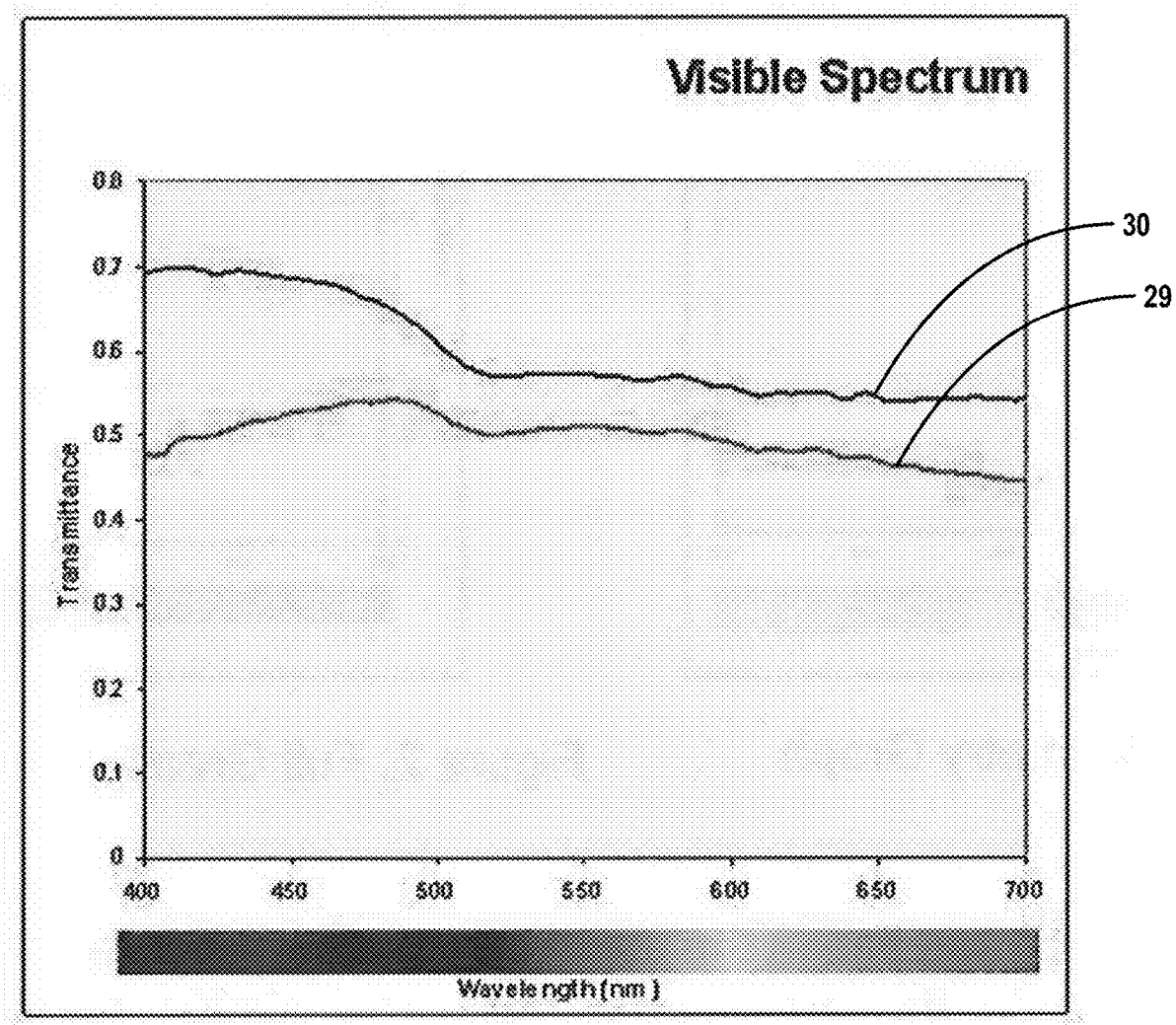
FIG. 3 illustrates the visual spectrum of light transmitted through the grease sample as compared to the spectrum of a base sample of the same type of grease.

The spectrum or color of the received light is compared to the spectrum or color received from a similar evaluation of a reference sample of grease at the same path length. FIG. 3 illustrates the spectrum 29 of the light received by the detector 16 as compared to the spectrum 30 of a reference or base sample of new, unused grease of the same type as the sample 20. The reference sample of grease, however, may be a different grease than that being evaluated since the reference services as a baseline for comparison. This is also valid as the sample being evaluated may commonly be a component of a mixture of more than one grease.

Darkening of the grease at an unexpected rate, for example, may indicate grease contamination or unexpected wear of machine components. It is anticipated that a library of grease spectra for different greases may be obtained over time that correlate to specific states or conditions of the grease measured or confirmed by other means and useful for grease analysis and troubleshooting. The library of spectra may be utilized by a machine learning algorithm, neural network, or other form of Artificial Intelligence for machine-generated evaluation of a grease sample using the data obtained from the spectrophotometer detector.

Figure 4:
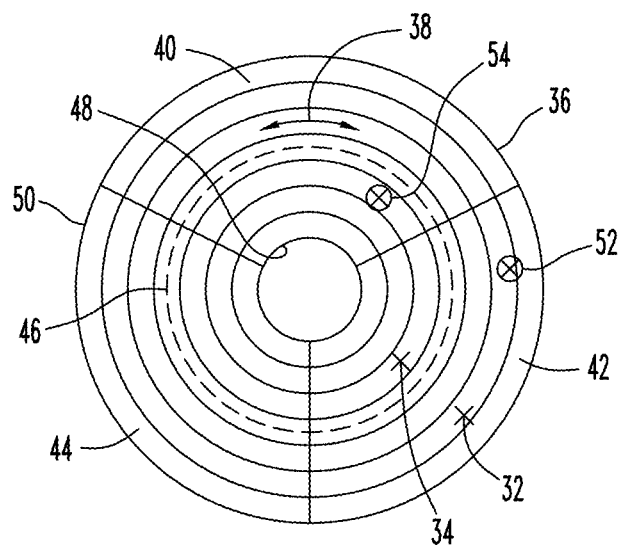
FIG. 4 illustrates the color of a sample of a first grease as compared to the color of a base sample of the same grease and the color of a sample of a second grease as compared to the color of a base sample of the same second grease, the colors determined by the device shown in FIG. 1.

FIG. 4 illustrates the measured color 32 of the grease sample 26 as compared to the measured color 34 of a reference sample of the same grease, the sheets 18, 20 being positioned to define the nominal gap 24b.

The colors are measured using the HWB (hue-whiteness-blackness) color space and are shown plotted on a color wheel 36, it being understood different color spaces can be used in other embodiments of the disclosed method. The illustrated color wheel distributes color hues circumferentially around the wheel as represented by the double arrow 38. To simplify the drawing of the color wheel only the range of green hues 40, range of red hues 42, and range of blue hues 44 are shown. Pure colors are on a circle 46; colors increasingly mixed with white move radially towards the inner circle 48 (which represents white) and colors increasingly mixed with black move radially towards the outer circle 50 (which represents black).

The grease sample color 33 is darker than the grease base color 34. The grease sample color has shifted radially towards the black circle 50, indicating darkening of the grease sample. The grease sample color has shifted relatively little circumferentially around the color wheel as compared to the base sample. That is, the grease sample has darkened but has not substantially changed hue as compared with the base sample.

Darkening of a grease sample color in comparison to the grease base color without a substantial change in hue typically indicates normal aging of the grease with time and use without contamination of the grease by solid particles, other greases or liquids, or other undesirable contamination agent or cause.

FIG. 4 also illustrates the color wheel 36 plotting the measured color 52 of a grease sample of a second, different grease as compared to the measured color 54 of a reference sample of the same grease.

The grease sample color 52 is darker than the grease base color 54. The grease sample color as compared to the base color has shifted radially towards the black circle 50, indicating darkening of the second grease sample. The grease sample color has also shifted circumferentially a relatively large amount around the color wheel as compared to the base color. That is, the second grease sample has darkened but has also substantially changed hue as compared with the base sample.

Substantial changes in hue of a grease sample color in comparison to the grease base color typically indicates contamination of the grease by solid particles, other greases or liquids, or some other contamination agent. That is, the second grease sample has darkened with time and use as expected. But the second grease sample has also substantially changed hue, indicating contamination or other undesirable, problematic agent of change.

Figure 5:
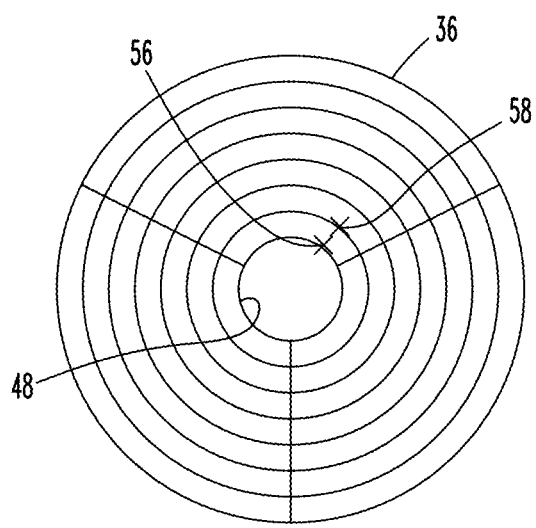
FIG. 5 is similar to FIG. 4 but illustrates the color of a sample of a third grease having a first thickness as compared to the same grease having a second, increased thickness, the colors determined by the device shown in FIG. 1.

FIG. 5 illustrates the same color wheel 36 being used to plot the measured color 56 of a grease sample of a translucent grease. The measured color 56 was also taken using the nominal sheet gap 24a. The measured color 56 is plotted very close to the inner white circle 48 of the color wheel. The measured color is essentially white, indicative of a bleached grease sample and does not provide useful and usable color and/or spectra information for evaluation.

The color measurement was taken again using the same grease sample but with the wider sheet gap 24c. Generally, a given grease sample is evaluated at different path lengths using successively narrower sheet gaps. It is usually not possible to increase the sheet gap due to the grease wanting to break adhesion with the sheets. If necessary another representative grease sample may be used if a later evaluation at a wider sheet gap is desired.

The measured color 58 using the wider gap is plotted radially outwardly from the measured color 48 and provides useful and usable color and/or spectra information for grease evaluation.

Figure 6:
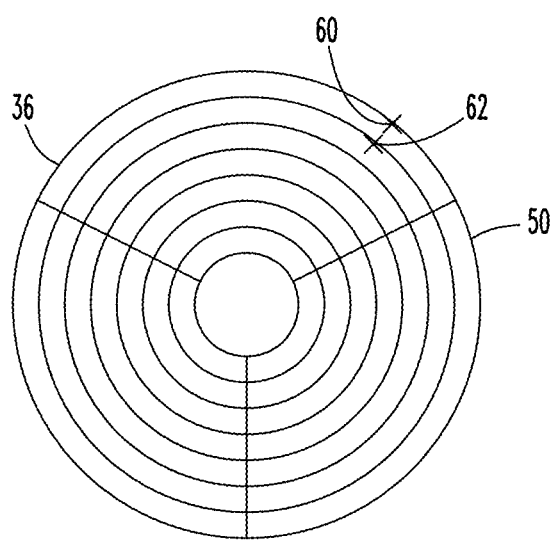
FIG. 6 is similar to FIG. 5 but of a fourth grease.

FIG. 6 illustrates the same color wheel 34 being used to plot the measured color 60 of a grease sample of a third grease. The measured color 60 was taken using the nominal sheet gap 24a. The measured color 60 is plotted very close to the outer black circle 50 of the color wheel. The measured color is essentially black, indicative of a grease that has gone black. The measured color does not provide useful and usable color and/or spectra information for grease evaluation.

The color measurement was taken again using the same third grease sample but with the narrower sheet gap 24b. The measured color 62 using the narrower gap is plotted radially inwardly from the measured color 60 and provides useful and usable color and/or spectra information for grease evaluation.

It is contemplated that a library of color and/or spectrum measurements for a grease may include measurements made with nominal sheet gaps as well as including measurements made with wider and/or narrower sheet gaps. A grease for example may require color or spectra measurement using a wide gap for new grease, a nominal gap for much of the operating life of a grease, and a narrow gap for when the grease has gone dark and is approaching the end of its useful life.

Figure 7:
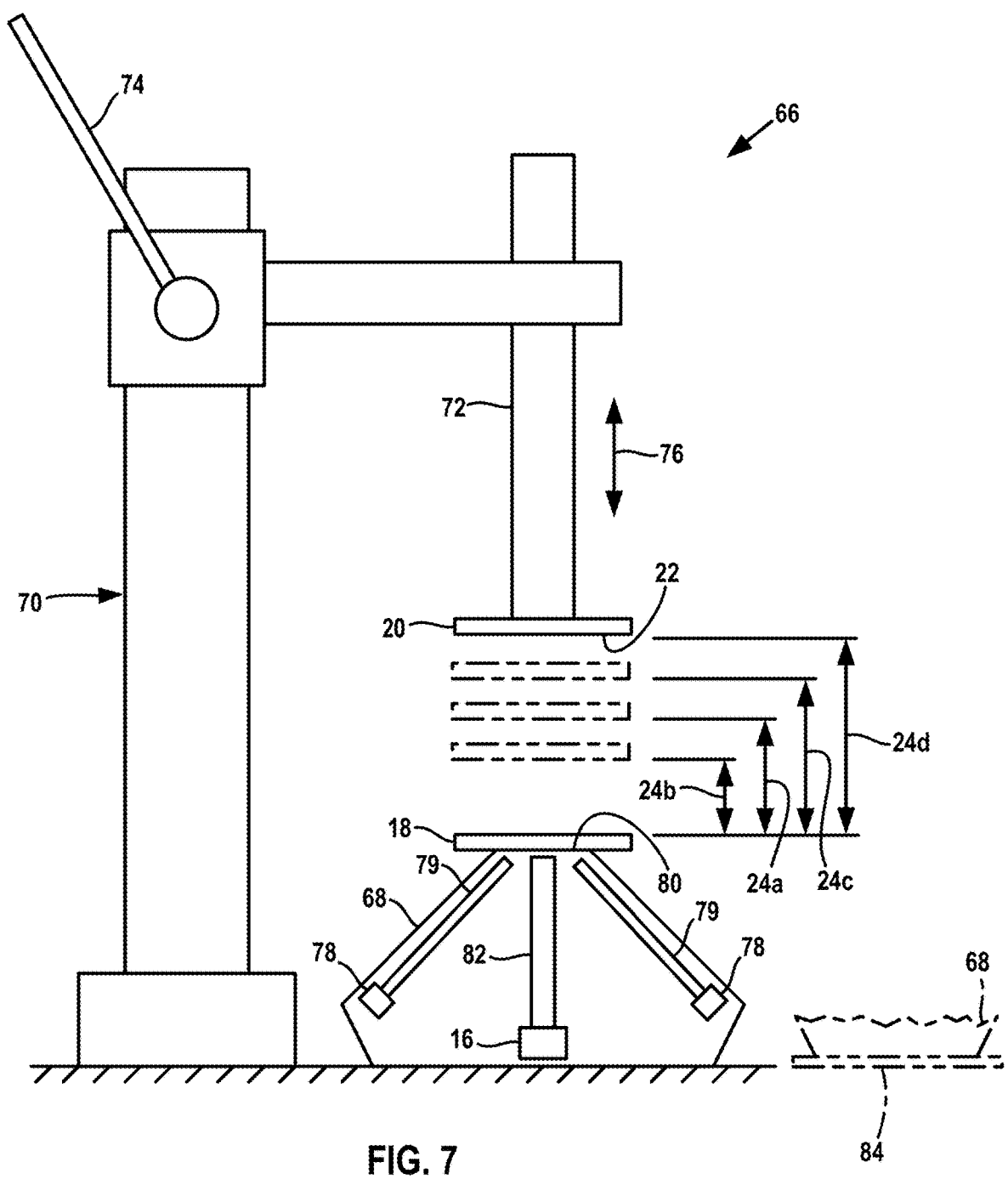
FIG. 7 illustrates an embodiment of the device shown in FIG. 1.

FIG. 7 illustrates an embodiment 66 of the device shown in FIG. 1 for carrying out a grease evaluation as disclosed herein. The transparent sheet 18 is mounted on a color sensor of the type disclosed in the Sheriden '109 patent. The reflective sheet 20 is mounted on an arbor press or lever press 70, the reflective surface 22 facing the color sensor. The arbor press and the color sensor are both supported on a table top.

The arbor press 70 has a manually movable ram 72 operable by a lever 74. The ram 72 is movable along a vertical stroke 76. The reflective sheet 20 is removably attached to the lower end of the ram by an adhesive (for example, double-sided tape) for conjoint movement with the ram.

The color sensor 68 is stationary and is located beneath the ram 72. The color sensor has a number of LED light sources 78 forming the light source of a spectrophotometer. Light from the LEDs is transmitted through light tubes 79 to emerge from the color sensor from a flat surface 80. Light is also received into the color sensor through the flat surface and is transmitted by an optical tube 82 to the light detector 16.

The color sensor disclosed in the Sheridan '109 patent is modified by centering the transparent sheet 18 on the top of the surface 80 of the color sensor 68. An additional thin sheet of transparent film (not shown) can optionally be placed between the transparent sheet and the sensor surface 80 to provide additional protection of the color sensor from contact with grease.

The color sensor 68 is positioned with respect to the arbor press 70 so that ram 72 is directly above the transparent sheet 18, the sheets 18, 20 being parallel and vertically aligned with one another. The reflective surface of the reflective sheet 20 faces the bottom of the ram 72.

The ram 72 is movable along its vertical stroke 76 towards and away the transparent sheet 18. The stroke length of the ram is adjustable so that the gap between the sheets 18, 20 can be set to the nominal gap 24a, the narrower gap 24b, or the wider gap 24c. The sheets are spaced apart by the largest gap 24d when the ram is at its highest, uppermost position along the stroke.

The stroke length of the ram is set for the desired gap distance 24. A grease sample is placed on the transparent sheet 20 and the ram is lowered to sandwich the grease sample between the sheets 18, 20. The grease sample is pressed between the sheets and comes into intimate contact with both sheets when the ram reaches its lowest position.

With the ram 72 in its lowered position the light source in the color sensor 68 transmits light through the grease sample and the spectrophotometer detects the reflected light that has passed again through the grease sample. The detector determines the color and/or the color spectrum of the grease sample from the detected light. The color data is transmitted from the color sensor to a data processing system (not shown) by wired or wireless transmission for data analysis and storage.

The gap 24 between the sheets 18, 20 can also be selectively varied by placing one or more shims 84 (shown in phantom in FIG. 7) or the like under the color sensor 68 to raise or lower the color sensor. This enables the ram 72 to hold the sheet 20 in a fixed position relative to the other components of the arbor press when evaluating a grease sample at different path lengths.

The grease evaluation device 66 is intended for manual operation. The arbor press is used primarily for its positioning and holding capability and not for generating press forces. In other possible embodiments of the device 66 the ram can form part of an electric linear actuator or similar actuator or positioning mechanism for selectively positioning of the sheet whereby the relative positioning of the sheets may be under automatic as well as manual control.

While this disclosure includes one or more illustrative embodiments described in detail, it is understood that the one or more embodiments are each capable of modification and that the scope of this disclosure is not limited to the precise details set forth herein but include such modifications that would be obvious to a person of ordinary skill in the relevant art and fall within the purview of the following claims.

What is claimed is:

1. A method for evaluating the condition of a grease, the method comprising the steps of:
    (a) placing a representative sample of grease on a first sheet;
    (b) placing a transparent second sheet in an overlaying relationship with the grease and the first sheet, the second sheet being spaced apart from and not in contact with the first sheet and thereby defining a gap containing the grease between the first and second sheets;
    (c) relatively displacing the second sheet towards the first sheet until the second sheet engages the grease but does not contact the first sheet and the grease effectively fills the gap between the first and second sheets;
    (d) passing light from a light source having an intensity through the second sheet and through the representative sample of the grease, the light traveling a first path length through the grease, the first path length associated with the gap between the first and second sheets;
    (e) detecting the light passed through the grease after the light has passed the first path length through the grease;
    (f) evaluating the detected light and determining that the intensity of the detected light is incapable of providing a meaningful analysis;
    (g) changing the gap between the first and second sheets by displacing the first sheet with respect to the second sheet while maintaining the second sheet spaced apart from and not in contact with the first sheet, the first and second sheets defining an increased or decreased gap filled with grease between the first and second sheets to associate a second path length associated with the increased or decreased gap between the first and second sheets, the second path length different from the first path length;
    (h) repeating steps (d)-(g) as needed without changing the intensity of the light source and having the light travel the second path length different from the first path length through the representative sample of the grease until the intensity of the detected light is capable of providing a meaningful analysis; and
    (i) quantifying the spectrum or color of the detected light having an intensity capable of providing a meaningful analysis and comparing the spectrum or color of the detected light with the spectrum or color of a reference sample of grease to quantify the differences between the spectrum or color of the representative sample of grease and the spectrum or color of the reference sample of grease.

2. The method of claim 1 wherein the second path length is greater than the first path length whereby the intensity of the detected light after traveling the second path length is less than the intensity of the detected light after traveling the first path length.

3. The method of claim 1 wherein the second path length is less than the first path length whereby the intensity of the detected light after traveling the second light path is greater than the intensity of the detected light after traveling the first path length.

4. The method of claim 1 wherein the first sheet has a reflective surface, the light passing through the representative sample of grease before being reflected off the reflective surface.

5. The method of claim 4 wherein the light reflected off the reflective surface passes through the representative sample of grease a second time before being detected.

6. The method of claim 1 wherein the step of passing the light through the representative sample of grease comprises the steps of passing the light a first time through the representative sample of grease, reflecting the light that has passed through the grease the first time, and passing the reflected light through the representative sample of grease a second time before the light is detected.

7. The method of claim 4 wherein the representative sample of grease in contact with the reflective surface.

8. The method of claim 1 wherein the second path length is greater than the first path length, and the representative sample of grease used with the first path length is a first portion of the grease being evaluated and the representative sample of grease used with the second path length is a second portion of the grease being evaluated that is different from the first portion.

9. The method of claim 1 wherein the second path length is less than the first path length, and the representative sample of grease used with the first path length is the same representative sample of grease used with the second path length.

10. The method of claim 1 wherein the step of quantifying the spectrum or color of the detected light comprises quantifying the color of the detected light using a color space.

11. The method of claim 10 wherein the color space is one of the following color spaces: HWB, HSL, LAB, XYZ, CIE, RGB, and CMYK.

12. The method of claim 1 wherein the step of quantifying the spectrum or color of the detected light comprises quantifying the color of the detected light by determining a PANTONE® unit.

13. The method of claim 10 wherein the step of quantifying the color of the detected light comprises quantifying the hue-blackness-whiteness of the color.

14. The method of claim 1 wherein comparing the spectrum or color of the detected light with the spectrum or color of a reference sample of grease comprises retrieving the spectrum or color of the reference sample from a library containing previous spectrum or color measurements of a reference sample of grease.

15. The method of claim 1 wherein the first sheet has a flat surface and the second sheet has a flat surface;

the step of placing a representative sample of grease on the first sheet comprises the step of placing the sample of grease on the flat surface of the first sheet;

the step of placing a transparent second sheet in an overlaying with the grease and the first sheet comprises the step of placing the flat surface of the second sheet in facing and parallel relationship with the flat surface of the first sheet, the flat surfaces of the first and second sheets thereby defining a uniform gap therebetween containing the grease.

16. The method of claim 15 wherein the step of changing the gap between the first and second sheets comprises maintaining the flat surfaces of the first and second sheets parallel with one another while displacing the first sheet with respect to the second sheet.

* * * * *